US00PP24874P3

(12) United States Plant Patent
Wheeler et al.

(10) Patent No.: US PP24,874 P3
(45) Date of Patent: Sep. 16, 2014

(54) BLUEBERRY PLANT NAMED 'BB05-61GA-61'

(50) Latin Name: *Vaccinium corymbosum*
Varietal Denomination: BB05-61GA-61

(71) Applicant: Berry Blue, LLC, Grand Junction, MI (US)

(72) Inventors: Edmund J. Wheeler, Holland, MI (US); James F. Hancock, East Lansing, MI (US)

(73) Assignee: Berry Blue, LLC, Grand Junction, MI (US)

( * ) Notice: Subject to any disclaimer, the term of this patent is extended or adjusted under 35 U.S.C. 154(b) by 55 days.

(21) Appl. No.: 13/651,256

(22) Filed: Oct. 12, 2012

(65) Prior Publication Data

US 2014/0109267 P1 Apr. 17, 2014

(51) Int. Cl.
*A01H 5/00* (2006.01)

(52) U.S. Cl.
USPC ..... Plt./157

(58) Field of Classification Search
USPC ..... Plt./157
See application file for complete search history.

(56) References Cited

U.S. PATENT DOCUMENTS

| | | | |
|---|---|---|---|
| PP9,834 | P | 3/1997 | Lyrene |
| PP10,675 | P | 11/1998 | Lyrene |
| PP11,807 | P2 | 3/2001 | Lyrene |
| PP11,829 | P2 | 4/2001 | Lyrene |
| PP12,165 | P2 | 10/2001 | Lyrene |
| PP15,103 | P3 | 8/2004 | Hancock |
| PP15,146 | P3 | 9/2004 | Hancock |
| PP16,333 | P3 | 3/2006 | Lyrene |
| PP16,404 | P3 | 4/2006 | Lyrene |
| PP18,138 | P3 | 10/2007 | Nesmith |
| PP19,503 | P3 | 11/2008 | Lyrene |
| PP20,027 | P3 | 5/2009 | Lyrene |
| PP21,881 | P3 | 4/2011 | Patel |
| PP22,692 | P3 | 5/2012 | Nesmith |
| PP22,778 | P3 | 6/2012 | Wright et al. |

*Primary Examiner* — Annette Para
(74) *Attorney, Agent, or Firm* — Graybeal Jackson LLP

(57) ABSTRACT

A new and distinct cultivar of blueberry plant named 'BB05-61GA-61' as described and shown herein. 'BB05-61GA-61' is a new and distinct low chill tetraploid Southern highbush (*Vaccinium*) variety of complex ancestry, based largely on *V. corymbosum* with some genes from *V. darrowii, V. angustifolium, V. tenellum* and *V. ashei.* It is a very productive early season ripening variety with very large size, small and dry picking scar, very firm fruit, and high quality fresh market characteristics. Fruit shape is oblate, color is medium blue with medium amounts of sugar and acidity and with a very crunchy and juicy texture. It has storage ability in refrigeration is at least 2 to 3 weeks.

4 Drawing Sheets

BACKGROUND AND SUMMARY

Blueberries are a well-known fruit enjoyed by many throughout the world. One example of an existing, patented blueberry variety is Star, U.S. Plant Pat. No. 10,675. Another example of an existing, patented blueberry variety is Rebel, U.S. Plant Pat. No. 18,138.

Compared to Star, the present cultivar, 'BB05-61GA-61', 50% of ripe fruit matures 5 days earlier. The 'BB05-61GA-61' has larger fruit that maintains consistent sizing through harvest, lighter blue color, larger fruit size, and a more rounded bush shape.

Compared to Rebel, 'BB05-61GA-61' has a more upright bush shape, lighter blue color, and a mean maturation date that is 5-7 days later. In 'BB05-61GA-61', the cluster density is tighter, time of bloom is a few days earlier, and the fruit quality, flavor, and firmness is much improved.

The present cultivar, 'BB05-61GA-61', provides one or more advantages compared to these and/or other blueberry varieties, such as one or more of earliness of ripening season, vigorous bush growth, large fruit size, and excellent fruit quality and flavor.

BRIEF DESCRIPTION OF THE PHOTOGRAPHS

DETAILED DESCRIPTION

Figure 1:
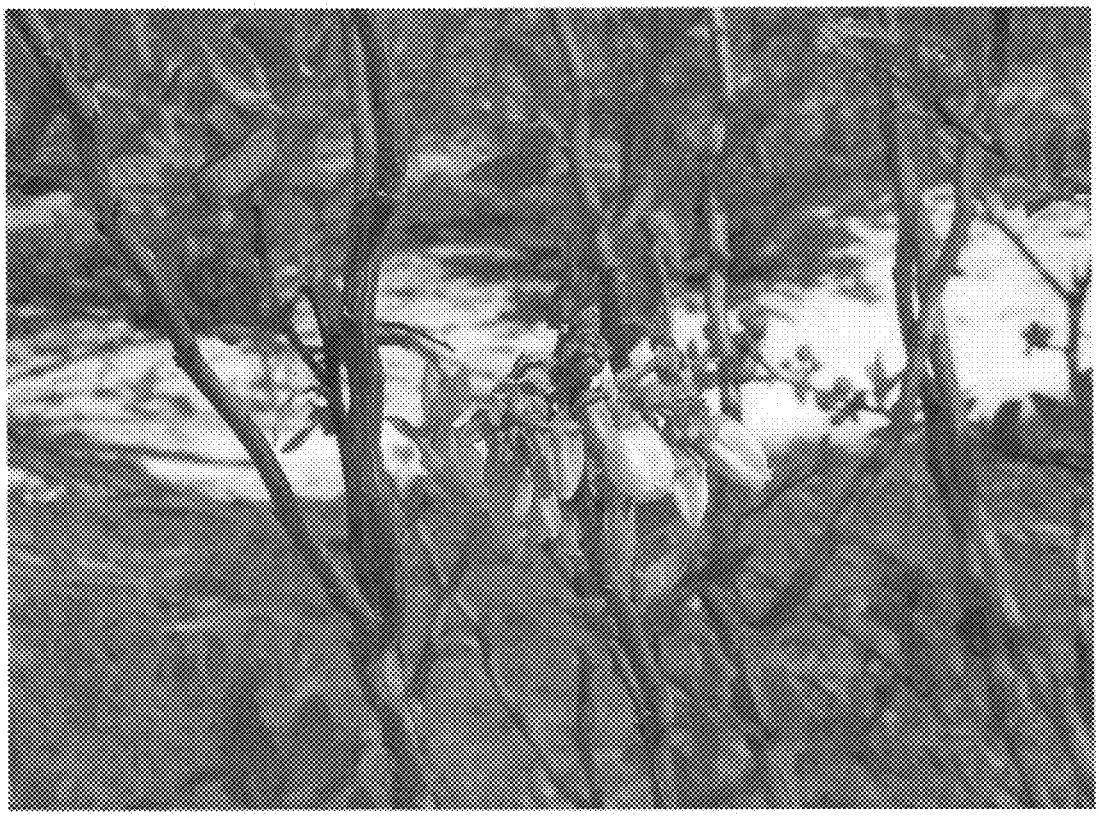
FIG. 1 is a photograph of the Blueberry cultivar 'BB05-61GA-61', showing unopened flower buds and open flowers as well as color, shape and size, expanding leaf buds.
Figure 2:
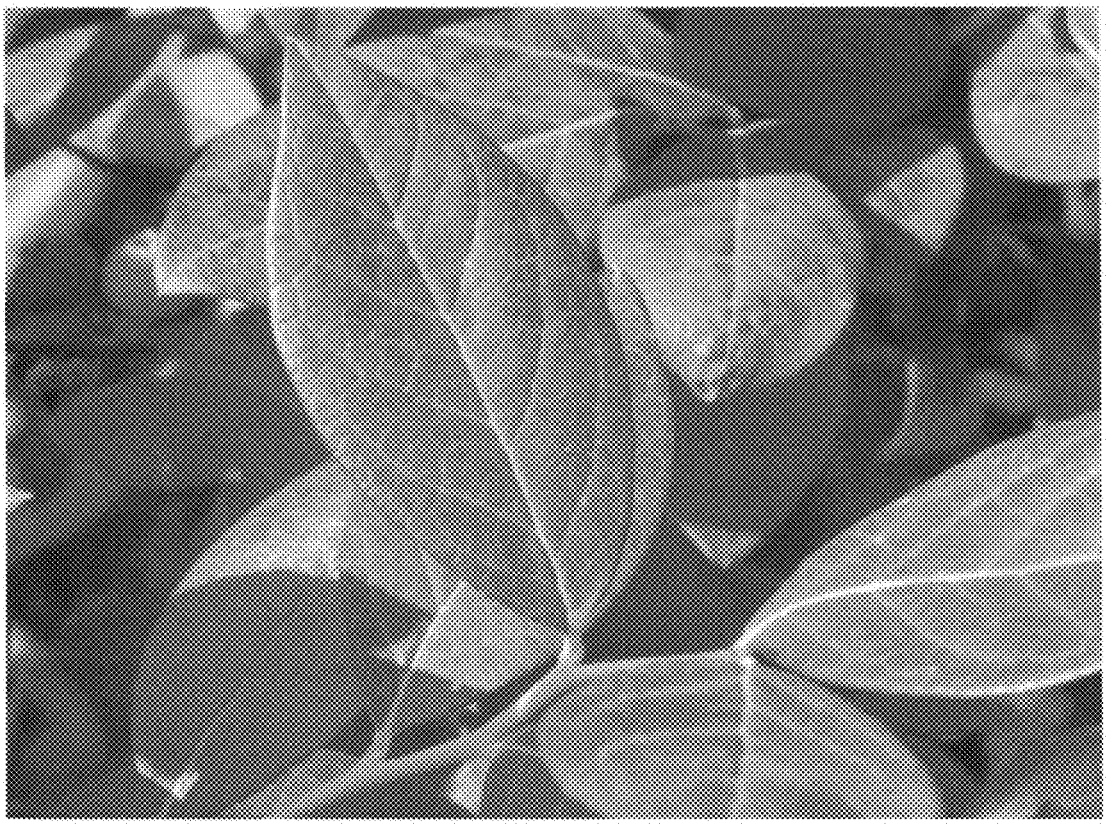
FIG. 2 is a photograph of the Blueberry cultivar 'BB05-61GA-61', is a close-up photo of mature leaves, and shows shape, color, venation, petiole size and coloration.
Figure 3:
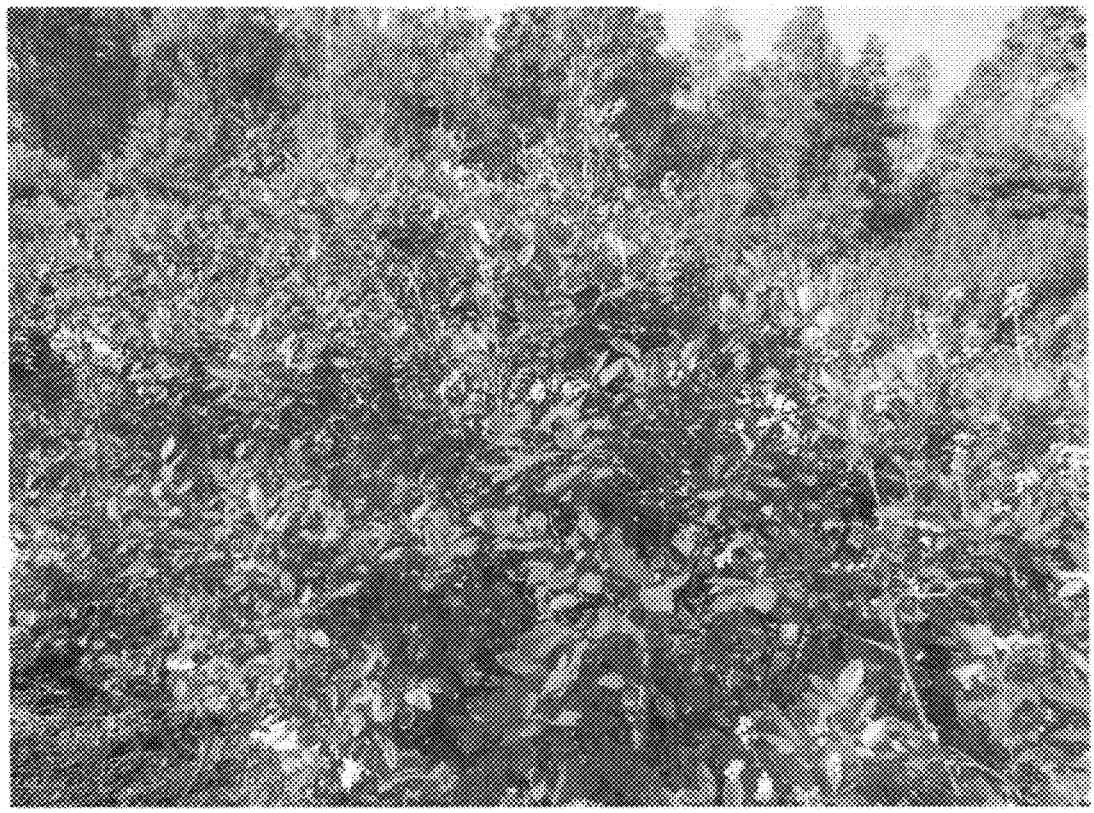
FIG. 3 is a photograph of the Blueberry cultivar 'BB05-61GA-61', showing an overall bush (center of photo), and thus showing bush shape, cane branching, and fruit presentation.
Figure 4:
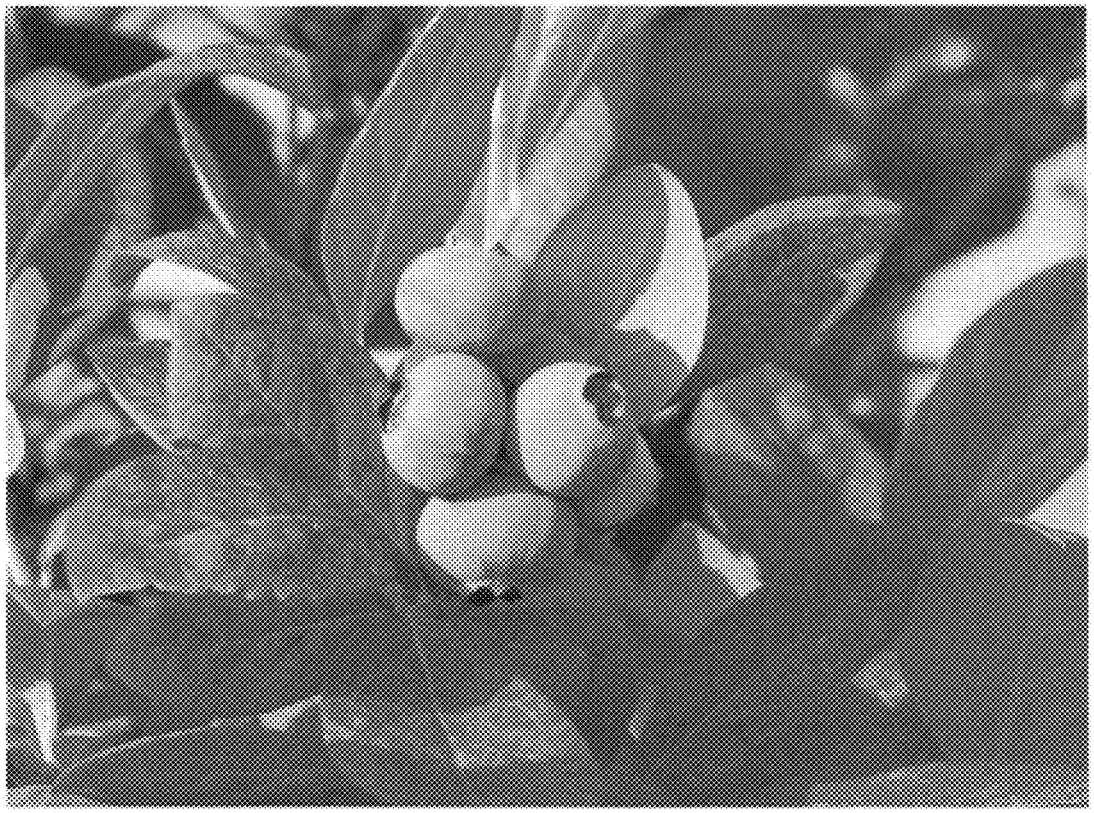
FIG. 4 is a photograph of the Blueberry cultivar 'BB05-61GA-61', is a close-up photo of ripe fruit, showing cluster density, color, size, calyx shape and ridging, mature leaves.

Note: statements of characteristics herein represent exemplary observations of the cultivar herein and will vary depending on time of year, location, annual weather, etc. Where dimensions, sizes, colors, and other characteristics are given, it is to be understood that such characteristics are approximations and averages. The descriptions reported herein are largely from specimen plants grown near Manor, Ga. Data were obtained on a plant that was 3 years old.

Cultivar name: 'BB05-61GA-61'.

Classification:

*Family.*—Ericaceae.

*Botanical name.*—*Vaccinium corymbosum.*

*Common name.*—Blueberry.

Parentage:

*Female parent.*—Name: Draper (Duke unpatented× G751 unpatented). U.S. Plant Pat. No. 15,103. Compared to Draper, Draper has much higher chill requirement (800 vs. 400) and is not adapted to a lower chill area production. 'BB05-61GA-61' has a more rounded bush shape than Draper, produces more canes than Draper, and matures 6-8 weeks earlier than Draper.

*Male parent.*—Jewel (parents unknown, unpatented). U.S. Plant Pat. No. 11,807. Compared to Emerald, 'BB05-61GA-61' has a higher chill requirement (400 vs. 250). BB05-61GA-61 has a mean maturation date that is 7-10 days later than Jewel, has a more flattened berry shape, and has a lighter blue color with a tighter cluster density.

'BB05-61GA-61' was created from a cross made in 2005 in a South Haven, Mich., greenhouse. Seeds from the cross were sown and plants were grown for 1 year in Grand Junction, Mich. and then planted in a seedling evaluation plot in 2006 near Manor, Ga. The plant was first selected in the spring of 2007 based on improved and excellent fruit and morphological characteristics. The individual bush was evaluated in successive years through 2009, exhibiting an excellent performance of earliness, very large berry size, and very good fruit quality. Several multi-bush trials were established near Interlachen, Fla., Manor, Ga., Homerville, Ga., and Baxley, Ga. in 2011. Two 250 bush plots were established in 2011 near Manor, Ga. In all of these bushes and trials, the characteristics of the original selection have been retained.

The cross for this variety was made in a South Haven, Mich., greenhouse in 2005. Seeds were sown and plants grown for approximately 1 year in Grand Junction, Mich. and resulted in 105 individuals of this cross.

'BB05-61GA-61' was first asexually propagated by softwood cuttings in Grand Junction, Mich., then planted in 2008 in evaluation trials in Grand Junction, Mich., Corvallis, Oreg., Interlachen, Fla., and Manor, Ga. In Michigan, 'BB05-61GA-61' did not prove to be sufficiently winter hardy and was discarded. In Florida, 'BB05-61GA-61' did not receive sufficient winter chilling to flower and fruit normally. 'BB05-61GA-61' was selected in the Manor, Ga. trial in 2010 based on excellent fruit and morphological characteristics, exhibiting excellent attributes such as maturity date, appearance, yield, and fruit quality. Additional plants have been propagated by softwood cuttings. A multi-bush trial was established near Manor, Ga. in 2012. The plants propagated have retained all of the characteristics of the original plant.

Field observations were made in Spring 2012 on a 3 year old plant located in a trial near Manor, Ga. propagated from the original selection. Laboratory analysis of fruit characteristics were done in Grand Junction, Mich.

'BB05-61GA-61' is a new and distinct low chill tetraploid Southern highbush (*Vaccinium*) variety, as illustrated and described, of complex ancestry, based largely on *V. corymbosum* with some genes from *V. darrowii, V. angustifolium, V. tenellum,* and *V. ashei*. It is a very productive early mid-season ripening variety with large size, small and dry picking scar, medium light blue color, very firm fruit, and high quality fresh market characteristics. It is intended for areas which successfully grow lower chill Southern highbush varieties. The fruit are large, typically 2 grams or more each, well exposed on a vigorous medium upright bush with a medium small crown. The mean date for 50% flowering in Southeast Georgia is about February 25. Winter chilling requirement for successful flowering and leafing is approximately 400 hours (<7° C.). Bush growth is vigorous. Flowering and leafing are synchronous. Frost protection may be needed for successful pollination and fruit set. Fruit are large in size with ripening of 50% of the fruit normally around May 1 in Southeast Georgia. Fruit shape is oblate, color is medium light blue with a medium-high amount of waxy bloom that is well retained and persistent following handling. The flavor is very good with a good balance of sweetness and acidity, and a very crunchy and juicy texture. Storage ability in refrigeration is at least 2 to 3 weeks. Thus, 'BB05-61GA-61' provides earliness of ripening season, vigorous bush growth, large fruit size, and excellent fruit quality and flavor.

References to color refer to The Pantone Book of Color, Eisemann and Herbert, Harry N. Abrams, Inc. Publishers, New York, ISBN 0-8109-3711-5, 1990.

No spectrographic device was used to take color readings.

Morphological characteristics reference: Plant Systematics, Jones and Luchsinger, 2 Ed., McGraw Hill, New York, ISBN 0-07-032796-3, 1986.

Average size information:

*General description.*—Medium large bush, medium upright shape, 3-year plant 139 cm height, 130 cm width, height/width ratio 1.1:1.

*Growth.*—Excellent.

*Productivity.*—Excellent.

*Cold hardiness.*—Leaf and flower buds −5° C., open flowers and fruit −2° C.

Specific features of the variety:

Plant:

*Growth habit.*—Medium upright.

*Plant width.*—132 cm at mid-bush.

*Plant height.*—139 cm.

*Spread.*—Canopy 132 cm.

*Productivity.*—5-6 lbs per mature bush.

*Cold hardiness/tolerance.*—Leaf and flower beds −5° C., flowers and fruit −2° C.

*Chilling requirement.*—400 hours below 7° C.

*Canes.*—Well branched, typically 8-9 canes/bush, 50-83 cm length, medium number of laterals. Mature cane color — Pantone Gravel, 14-1014. Texture — rough.

*Fruiting wood.*—Smooth, immature winter color — Pantone Marsala 18-1438; immature summer color — Pantone Boa 17-0625.

*Internode length range.*—12-20 mm, average 18 mm.

*Surface texture of new wood.*—Smooth.

*Mature canes.*—Circular, 17 mm width.

*Time of beginning of leaf bud burst (include location(s)).*—February 15 (Manor, Ga.).

*Time of beginning of flowering (include location(s)).*—February 20 (Manor, Ga.).

*Time of fruit ripening (include location(s)).*—May 1 (Manor, Ga.).

*Disease resistance/susceptibility.*—None claimed.

Foliage:

*Leaf color.*—Upper — Pantone Chive 19-0323; lower — Pantone Tea 16-0213.

*Leaf arrangement.*—Alternate, shape — elliptic.

*Leaf margins.*—Entire.

*Leaf venation.*—Pinnate.

*Leaf apices.*—Acute.

*Leaf bases.*—Acute.

*Vein and petiole colouration.*—Pantone Green Oasis 15-0528.

*Petiole length.*—5 mm.

*Leaf dimensions*.—Overall shape: 60 mm-72 mm range, average 65 mm. Width: 35 mm-40 mm range, average 38 mm.

*Leaf margins*.—Entire; no visible pubescence or nectaries.

*Leaf surface*.—Upper — small hairs on midrib; Lower — none.

Flower:

*Flower shape*.—Elongate urceolate.

*Flower bud number*.—Medium high.

*Flowers per cluster*.—8.

*Flower fragrance*.—Light floral.

*Corolla color*.—Pantone Bone White 12-0105.

*Corolla length*.—10-11 mm.

*Corolla aperture width*.—4-5 mm.

*Flower peduncle*.—4 mm.

*Color*.—Pantone Chive 19-0323.

*Flower pedicel*.—6 mm.

*Color*.—Pantone Chive 19-0323.

*Calyx* (*with sepals*).—2 mm.

*Color*.—Pantone Chive 19-0323.

*Stamen*.—Length: 8 mm.

*Number per flower*.—10.

*Filament color*.—Pantone Baked Clay 18-1441.

*Style*.—9 mm.

*Color*.—Pantone Willow Green 15-0525.

*Pistil*.—8 mm, from top of ovary to stigma tip.

*Ovary color*.—Pantone Willow Green 15-0525.

*Anther*.—Length: 3 mm.

*Number*.—10/flower.

*Color*.—Pantone Baked Clay 18-1441.

Pollen:

*Abundance*.—Medium high.

*Color*.—Pantone Antique White 11-0105.

Fruit:

*Date of* 50% *maturity*.—May 1 (Manor, Ga.).

*Yield*.—5-6 lbs/bush.

*Berry color*.—With wax: Pantone Silver Blue Lake 17-4030. With wax removed: Pantone Purple Velvet 19-3725.

*Berry flesh color*.—Pantone Frozen Dew 13-0513.

*Berry surface wax abundance*.—Medium-heavy, persistent.

*Calyx*.—Width — 5 mm; depth — 2 mm; shape — 5 lobed with small ridges.

*Berry weight*.—2.3 grams/berry.

*Berry size diameter*.—18 mm width, 13 mm height, Aspect (H/W) — 0.7.

*Berry shape*.—Oblate.

*Fruit stem scar*.—Small (>1 mm), dry.

*Cluster density*.—Medium.

*Detachment force*.—Easy.

*Self-fruitfulness*.—Fair; will need cross pollination for maximum yield, earliness, and size.

*Berry firmness*.—Firm, FirmTec 2 score — 196 g/mm$^2$.

*Berry sweetness*.—Medium Brix° 11.6.

*Berry acidity*.—Medium, TA — 0.54.

*Berry flavor and texture*.—Very good with balanced sweetness and acidity, crunchy and juicy.

*Suitability for mechanical harvesting*.—Possible because of bush shape, crown size, firmness, detachment, and cluster density.

Seed:

*Seed abundance in fruit*.—Medium.

*Seed color*.—Pantone Topaz 16-1150.

*Seed dry weight*.—NA.

*Seed size*.—Medium — 1 mm.

Possible typical market uses: Fresh market, processing into jams, puree, yogurt.

Storage quality: Medium, at least 2-3 weeks in refrigerated storage.

What is claimed is:

1. A new and distinct cultivar of Blueberry plant named 'BB05-61GA-61' as described and shown herein.

* * * * *